(12) United States Patent
Voss et al.

(10) Patent No.: US 7,842,481 B2
(45) Date of Patent: Nov. 30, 2010

(54) METHOD FOR PRODUCING EXTRA-CHROMOSOMAL NUCLEIC ACID MOLECULES

(75) Inventors: Carsten Voss, Lage (DE); Erwin Flaschel, Bielefeld (DE)

(73) Assignee: Plasmid Factory GmbH + Co. KG, Bielefeld (DE)

( * ) Notice: Subject to any disclaimer, the term of this patent is extended or adjusted under 35 U.S.C. 154(b) by 66 days.

(21) Appl. No.: 11/120,812

(22) Filed: May 3, 2005

(65) Prior Publication Data

US 2005/0244947 A1 Nov. 3, 2005

(30) Foreign Application Priority Data

May 3, 2004 (DE) ........................ 10 2004 021 787
Oct. 27, 2004 (DE) ........................ 10 2004 052 254

(51) Int. Cl.
*C12P 19/34* (2006.01)
*C12Q 1/68* (2006.01)
*C12M 1/33* (2006.01)
*C07H 21/00* (2006.01)

(52) U.S. Cl. .................. 435/91.1; 435/6; 435/306.1; 536/25.4

(58) Field of Classification Search .................. None
See application file for complete search history.

(56) References Cited

U.S. PATENT DOCUMENTS 5,407,426 A * 4/1995 Spears .......................... 604/24
2005/0026177 A1* 2/2005 Urthaler et al. ................ 435/6
2005/0079534 A1* 4/2005 Warthen et al. ................ 435/6

FOREIGN PATENT DOCUMENTS

WO WO 03102184 A1 * 12/2003
WO WO 2004024283 A2 * 3/2004
WO WO 2004108260 A2 * 12/2004

OTHER PUBLICATIONS

Theodossiou et al. Methods of enhancing the recovery of plasmid genes from neutralised cell lysate. Bioprocess Engineering (1999) 20: 147-156.*

* cited by examiner

*Primary Examiner*—Young J Kim
*Assistant Examiner*—Angela M Bertagna
(74) *Attorney, Agent, or Firm*—Stacey J. Farmer; Grund IP Group

(57) ABSTRACT

The present invention relates to a method, whereby microbial cells are broken up and cellular components are separated and an apparatus suitable for carrying out the method. Preferably, the cells contain extra-chromosomal nucleic acids that are released and are further suitable for additional purification as required for any pharmaceutical or technical use.

20 Claims, 2 Drawing Sheets

METHOD FOR PRODUCING EXTRA-CHROMOSOMAL NUCLEIC ACID MOLECULES

RELATED APPLICATIONS

This application claims the benefit of priority of German patent applications DE 10 2004 021 787.4 filed on May 3, 2004 and DE 10 2004 052 254.5 filed on Oct. 27, 2004. Each of the aforementioned applications are explicitly incorporated herein by reference in their entirety and for all purposes.

FIELD OF THE INVENTION

The present invention relates to a method of producing extra-chromosomal nucleic acid material. Specifically, a clear lysate containing extra-chromosomal nucleic acid is produced by separating unwanted cellular components (e.g. cell debris, proteins, genomic DNA) by flotation. The clear extra-chromosomal nucleic acid containing lysate can be readily produced within a short time and in large volumes and is further useful for isolating biologically active ingredients, such as plasmid DNA, for pharmaceutical applications (e.g. formulations). Furthermore, a continuous production of clear extra-chromosomal nucleic acid containing lysate, including plasmids, is possible with minimal disruption to the chromosomal material.

BACKGROUND OF THE INVENTION

Nucleic acids as a biotechnological product are becoming increasingly important since they are often used as a therapeutic substance for the treatment of diseases (i.e. gene therapy) or as a means of protection from infectious diseases (i.e. genetic immunization). In the field of non-viral gene transfer, the genetic information contained within the polynucleotide is typically transferred into the target cell as a vector, either in a pure form ("naked DNA") or alternatively as a complex, e.g. associated with other substances (including lipids, liposomes, PEI, carboplexes, proteins, gold particles, vesicles, nano-containments or magnetic beads) to either protect the nucleic acid or release it in a particular way or to target the nucleic acid to specific cells, where the gene expression should occur.

For the production of the nucleic acids, standard microorganisms are typically used that replicate extra-chromosomal circular nucleic acids. Common examples of such nucleic acids include plasmids, cosmids, BACs (bacterial artificial chromosomes), YACs (yeast artificial chromosomes) or MACs (mammalian artificial chromosomes).

The microorganisms are then cultivated to a high cell density with a maximum yield of the desired nucleic acid. In some applications, the desired extra-chromosomal nucleic acid might be a modified product (e.g. a mini-circle deriving from a plasmid vector, known collectively as "nucleic acid" or "plasmid"). For the isolation of the nucleic acid, the cells have to be broken up (e.g. disrupted, extracted, lysed). For this purpose, different physical and chemical processes are known. The major goal of such processes is to obtain a high yield of nucleic acid and to have the capacity to perform any subsequent purification steps using the simplest means possible.

For the isolation of plasmid DNA, alkaline lysis, a well-known chemical extraction procedure is usually applied (see Birnboim, H. C., Doly, J. (1979), A Rapid Alkaline Extraction Procedure for Screening Recombinant Plasmid DNA, Nucl. Acid. Res. 7, 1513-1523). In this procedure, suspended cells are lysed using an alkaline extraction reagent. During the neutralization step, the lysate is neutralized with an acidic potassium acetate solution, whereby proteins, chromosomal DNA and cell debris flocculate together with potassium dodecyl sulphate. Plasmid DNA (i.e. nucleic acid) remains within the resulting solution and can be separated from the majority of the flocculated contaminants.

The use of nucleic acids in pharmaceutical or technical applications (e.g. gene therapy, nucleic acid vaccination, or product labeling) requires a manufactured yield in gram and kg amounts; in the case of market supply, even larger scale production is required. For laboratory use and pilot scale, the alkaline lysis is normally performed as a batch process. However, this process is not simply scalable. Due to local pH peaks, the nucleic acid might be irreversibly denatured or the extraction is incomplete, both of these effects can result in low product yield or contaminated forms of nucleic acids that are difficult to separate from the intended product.

A further problem of known alkaline lysis techniques is the separation of cellular components. Due to a typical high viscosity of the resulting precipitate, separation can only be performed by pre-filtration or centrifugation and then subsequent clearing filtration. This approach is time consuming and expensive. Furthermore, the DNA (chromosomal DNA as well as plasmid DNA) within the precipitate is sensitive to shearing forces (see Levy, M. S. et al. (2000), Biochemical Engineering Approaches to the Challenges of Producing Pure Plasmid DNA. *Trends Biotechnol.* 18, 296-305). Therefore, an approach to gently mix the cell lysate and the neutralizing agent in the presence of low shear forces is necessary to avoid contaminating the plasmid containing liquid with chromosomal DNA that can not be easily removed.

In one known extraction procedure, a cell suspension and lysis buffer are pumped into a lysis vessel and the mixing is performed by a stirrer (see Wright, J. L. et al, (2001), Extraction of Plasmid DNA Using Reactor Scale Alkaline Lysis and Selective Precipitation for Scalable Transient Transfection, *Cytotechnol.* 35, 165-173). After subsequent addition of the neutralizing buffer, the precipitate is then separated from the product (i.e. plasmid) containing liquid. In this process, high concentrations of chromosomal DNA fragments having different sizes are generated due to high shear forces. Such fragments can not easily be separated from the plasmids and are only be detectable via polymerase chain reaction (PCR) analysis.

Another known process requires pumping a cell suspension stream and a lysis buffer stream into a static mixer (see Wan, N. C. et al. (1997), Method for Lysing cells, U.S. Pat. No. 5,837,529). The resulting lysate is then introduced into a second static mixer and mixed with the neutralization buffer. The precipitate generated by this approach must then be separated from the product (plasmid) containing liquid in an expensive and time consuming way, as described above. This technique does avoid any local pH peaks generated through continuous mixing. However, since the shear sensitive neutralization is also performed by a static mixer, the pressure decline over the mixer at this stage in the procedure also leads to shearing of DNA, resulting in a high contamination of the product stream.

In an additional procedure, pH peaks are avoided by mixing small volumes of cell suspension and extraction reagents at a time (see Chevalier, M. (1999), Method and Device for Cell Lysis, CA 0002 31 9021 A1). In this case, mixing is not achieved by using a static mixer but rather by the fast collision of cell suspension and extraction reagents, preferably in stream channels directed towards each other at a right angle. In this process, the diameter of the channel diameter is reduced to 2 from 8 mm, to achieve sufficient mixing. The consequence of this reduction in diameter is that an extracted lysate can only be processed at a maximum speed of 160 mL per minute. Since the neutralization step is also performed in this manner, a high shear force is likewise applied to the precipitated cellular components.

An additional method relates to a non-rigid, gentle mixing of the extracted cell mass with the neutralization buffer, thereby introducing the neutralization buffer into the cell lysate together with air (see Ciccolini, L. A. S. et al. (1999), Rheological Properties of Chromosomal and Plasmid DNA During Alkaline Lysis Reaction. *Bioproc. Eng.* 21, 231-237).

For the separation of the precipitated cell components, one method utilizes the low density of the flocculated cell components, wherein such components generally float to the surface of the liquid after a relatively long incubation time (see Theodossiou, I. et al. (1999), Methods for Enhancing the Recovery of Plasmid Genes from Neutralised Cell Lysate. *Bioproc. Eng.* 20, 147-156). However, this process requires longer than one hour due to the only minor difference in the buoyancy of the precipitate compared to the liquid. Thus, the resulting yield using this technique is heavily restricted. Another disadvantage of this method is the necessary and subsequent clear filtration step before any further chromatographic purification of the nucleic acid.

In the present state of the art, there is no known technique whereby the cells are extracted in a gentle way to reduce shearing forces, where the cellular components are separated in a way to avoid contamination of the product stream when the separation of precipitate and product containing liquid stream is rapid. Such a technique would be useful in generating high yields of nucleic acids, without the requirement for any subsequent treatment of the obtained lysate for additional purification (e.g. chromatography or precipitation).

SUMMARY OF THE INVENTION

The present invention describes a method for the production of a clear extra-chromosomal nucleic acid containing lysate from a cell solution by separating unwanted cellular components (e.g. cell debris, proteins, genomic DNA) in a gentle and non-disruptive manner. The separation is based on the principle of flotation, i.e. the separation of the precipitate from the clear lysate by adsorption to gas bubbles, which allows for a maximal reduction of shear forces on the nucleic acids and thus a gentle and cost-effective separation requiring minimal equipment. Furthermore, a continuous production of clear extra-chromosomal nucleic acid containing lysate is disclosed as well as an apparatus suitable to carry the presently claimed method. It will be clear to the skilled person in the art that the method of the present invention may be applied not only to the exemplified microbial cells but also to any other cell type (e.g. eukaryotic cells such as plant, animal, mammalian or human cells) comprising extra-chromosomal nucleic acids.

Initially, cells are suspended in an appropriate liquid. The mixing of this suspension with an extraction buffer for lysing the cells is achieved by mixing both liquids in such a way that the main effect takes place within a small volume (or "mixing point"). The extraction reaction occurs within a tubing or pipeline volume which starts immediately subsequent to (or "downstream" to) the mixing point. The subsequent separation of the flocculated cellular components is achieved through flotation within a column filled with neutralizing buffer. During this flotation step, both a rapid solid-liquid separation and a gentle separation of the precipitate of the neutralization is realized.

Using the present method, an additional further purification of the clear lysate via a subsequent chromatographic separation, precipitation or other product purification is not necessary. However, if a further purification of the obtained clear lysate is desired, such purification may be carried out according to purification methods known in the art. Thus, after collecting the plasmid-containing clear lysate from the vessel of the method as presently claimed, purification by chromatography, by precipitation using silica, or using CTAB fractional precipitation (as described inter alia in WO 01/46215) is possible.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
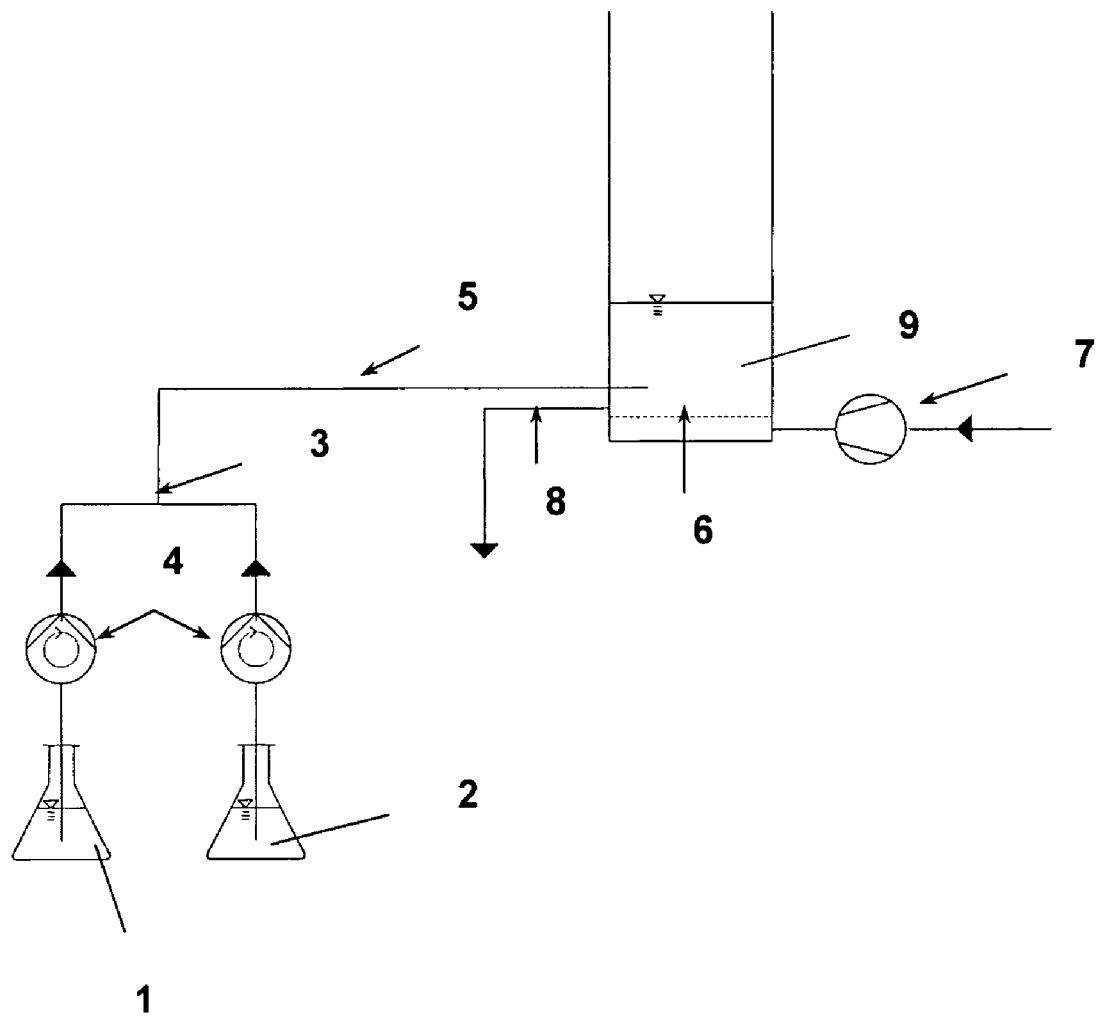
FIG. 1 is a schematic illustration showing an apparatus suitable for the gentle isolation of clear lysate from a cell suspension containing extra-chromosomal nucleic acids.

As used herein, the term "flotation" means a liquid-solid separation approach whereby a gas is dispersed in a suspension and the suspended solid then adsorbs at the gas bubbles and collects in a foam layer (i.e. foam flotation) (see D. Schlee and H.-P. Kleber, Biotechnologie, Gustav Fischer Verlag, Jena).

As used herein, the term "volume element" means any device that can be used to contain a substance in its interior and through which said mixture may migrate or flow during the reaction. Such a volume element comprises at least two ports, preferably located at opposing ends of the device. Examples for such a volume element, include but is not limited to, tubes, hoses, columns or pipelines made of any suitable material.

As used herein, the term "mixing point" means a preferably small volume element having at least two inlets and at least one outlet for a substance (in liquid or gas form). In a preferred embodiment, the mixing point has the form of a "T" (T-mixer), wherein the inlets are opposing each other at an angle of 180° and the outlet is located perpendicular to and between the two inlets.

As used herein, the term "extra-chromosomal nucleic acids" means any nucleic acid that may be found in a cell that is not part of the chromosomal material of the cell, i.e. not genomic DNA. Examples of extra-chromosomal nucleic acids include plasmid DNA, chloroplast DNA or mitochondrial DNA, cosmids, BACs, YACs, MACs, mini-plasmids or mincircles.

As used herein, the term "microorganism" means any bacterial cell or a single eukaryotic cell including, e.g., yeast or single plant or animal cells. The term "microbial" refers to microorganisms.

As used herein, the term "cell suspension" means any suspension of microorganisms in a liquid. Such a cell suspension may thus contain bacterial cells as well as eukaryotic cells including yeast or single plant or animal cells.

As used herein, the term "lysate" means a solution of broken up cells, i.e. cells whose cell membrane and/or cell wall has been broken up by any means, including physical, chemical or biological means.

As used herein, the term "vector" means in its broadest sense a nucleic acid construct that has the ability to be replicated and may carry additional genetic information.

The clarity of a liquid can be determined by numerous techniques, including scattered light measurement (optical density, OD) using a photometer in an absorption modus where a wavelength of 600 nm versus water is determined as the reference. A cell lysate is called "clear" when an $OD_{600}$ of maximum 0.05 E/cm is detected (see Schumacher et al. (2002), WO 02/057446 A2).

In one aspect of the present invention, a method is disclosed by which a gentle purification of extra-chromosomal nucleic acid containing clear lysate of a cell suspension from unwanted cellular components is provided. Such purification relates to the separation of unwanted cellular components such as e.g. proteins, lipids, polysaccharides, genomic (chromosomal) DNA, and proteins from a mixture of cell suspension and extraction buffer to produce a clear lysate of the cell suspension. The cell suspension may comprise any type of extra-chromosomal nucleic acid comprising cells, eukaryotic or prokaryotic, that have been dissolved in a suitable liquid, e.g. a cell culturing medium, TRIS, TBS (TRIS buffered saline), or PBS (phosphate buffered saline). Such extra-chromosomal nucleic acid can, for example, be plasmid DNA, mitochondrial DNA, chloroplast DNA, cosmids, BACs, YACs, MACs, mini-plasmids or mincircles. In a preferred embodiment of the invention, the cells have been transfected with a vector. In a further aspect of the invention, the cells are Gram-positive or Gram-negative bacterial cells. The cells are produced by known cultivation processes and can be stored frozen or used directly for the extraction process following removal or replacement of the cultivation medium by a liquid.

In a first step of the present method, the cell suspension and an extraction buffer are mixed together. The extraction buffer belongs to the group of an alkaline solution, detergents, enzymes or organic solvents as well as combinations thereof and the mixing preferably occurs in a mixing point. An exemplary extraction buffer includes a solution of 200 mM NaOH and 1% SDS. A mixing point is a preferably small volume having at least two inlets for the cell suspension and the extraction buffer, respectively, and at least one outlet for the mixture to flow through. In a preferred embodiment, the mixing point comprises a "T" form (T-mixer), wherein the inlets are opposing each other at an angle of 180° and the outlet is located perpendicular to and between the two inlets. The T-mixer facilitates an effective mixing of the cell suspension and the extraction buffer so that the flow rates of the two liquids can be reduced or kept at low values (e.g. a linear flow rate of 830 cm total per minute), thus leading to diminished shearing forces. In another embodiment, the cell suspension and the extraction buffer are transferred into the mixing point via pumps.

In a second step of the present method, the mixture of cell suspension and extraction buffer is contacted for a reaction time sufficient to adequately disrupt the cells. This reaction time depends on the cell-type and the type of extraction buffer used, and can readily be determined by one of ordinary skill in the art. In a preferred embodiment, the mixture is reacted for a time of 0.27 minutes, in a more preferred embodiment the mixture is reacted for a time of 0.5 minutes and in an even more preferred embodiment, the mixture is reacted for a time of more than 1 minute.

In one aspect of the method of the present invention, the reaction is carried out in a volume element directly connected to the outlet of the T-mixer. The use of said volume element facilitates a continuous and gentle reaction of the cell suspension and the lysis buffer as the mixture advances along the volume element. In a preferred embodiment, the mixture advances within the volume element at a linear flow rate of between 250 and 1400 cm per minute, preferably between 280 and 900 cm per minute. A volume element can include any device that can be used to contain the mixture in its interior and through which said mixture may migrate or flow during the reaction. Examples for such a volume element, include but are not limited to, tubes, hoses, columns or pipelines made of any suitable material. In a preferred embodiment, the volume element is a tube, column or pipeline having a diameter of 1.1 cm, 1.2 cm, 1.3 cm, 1.4 cm, 1.5 cm, 1.6 cm, 1.7 cm, 1.8 cm, 1.9 cm, 2 cm, or greater than 2 cm. In a more preferred embodiment, the diameter of such volume element is between 1.2 and 1.6 cm.

In a further step of the present method, the reaction mixture is brought into contact with a neutralizing buffer. The neutralizing buffer may be any solution that facilitates adjustment of the pH of the reaction mixture to a value that results in the precipitation of the unwanted cellular components, e.g. comprising genomic DNA and proteins to form a precipitate. Such a neutralization buffer may, for example, be a 3 M solution of potassium acetate and acidic acid having a pH of 5.5.

In a preferred embodiment, the mixing step is carried out in a vessel, such as a column or a HPLC column that contains the neutralization buffer. Furthermore, the vessel comprises a means at its bottom providing for the generation of small gas bubbles if gas is dispersed through said means. Such means for the generation of gas bubbles may be any porous substance, including a sintered substance.

Moreover, in another embodiment of the invention, the means for generating gas bubbles is a frit, a HPLC sieve or a sintered filter element. In a further preferred embodiment of the invention, the means for the generation of gas bubbles is a frit, or a sintered filter element having an apparent pore diameter selected from the group consisting of 0.5 µm, 1 µm, 3 µm, 5 µm, 10 µm, 15 µm, 20 µm, 30 µm, 40 µm, 50 µm, 80 µm, 100 µm, 150 µm, 200 µm, 250 µm, 300 µm, 350 µm, 400 µm, 450 µm, 500 µm, 750 µm and less than 1000 µm. In an even more preferred embodiment of the invention, the diameter is 0.5 µm or 200 µm.

The gas used to generate the gas bubbles may be any suitable gas known to the person skilled in the art. In a preferred embodiment, the gas is nitrogen, oxygen, carbon dioxide, inert gases, or a combination thereof. The gas bubbles may be introduced into the vessel either prior to or in parallel with the mixture to be transferred from the volume element to the vessel.

As described in the presently claimed method, the precipitate will adsorb to the gas bubbles, and will ascend or float in the neutralizing buffer to form a foam layer on top of the neutralizing solution, while the extra-chromosomal nucleic acid stays in solution within the clear lysate in a process known as "flotation". Thus, the precipitate is thereby separated from the clear lysate containing the extra-chromosomal nucleic acid.

In a preferred embodiment, the vessel containing the neutralizing buffer comprises at least one inlet for the reaction mixture and at least one outlet for the clear lysate comprising extra-chromosomal nucleic acid in the bottom region of the vessel. In another preferred embodiment, the volume element of the second step of the present method is directly connected to the T-mixer and one or more of the inlets of the vessel containing the neutralizing buffer.

In a further step of the presently claimed method, the clear lysate comprising the extra-chromosomal nucleic acid is collected from the vessel containing the neutralizing buffer. In a preferred embodiment, the collecting of the clear lysate is carried out by pumping the clear lysate through the outlet.

According to the present invention, under the conditions of a linear flow rate of between 250 and 1400 cm per minute and an incubation time within the volume element of at least 0.27 minutes, a plasmid concentration within the clear lysate can be achieved that is comparable to one of a manually prepared clear lysate. Surprisingly, the clear lysate produced by the presently claimed method shows a high degree of clarity ($OD_{600}$=0.002) in comparison with a manually prepared clear lysate ($OD_{600}$=0.03).

Surprisingly, the clear lysate achieved by the present method can be applied to any further purification step (e.g. chromatography or precipitation) without any additional treatment. An additional further purification of the clear lysate for a subsequent chromatographic separation, precipitation or other further product purification is not necessary. However, if a further purification of the obtained clear lysate is desired, such purification may be carried out according to purification methods known in the art.

The method of the present invention may be carried out continuously, thus allowing for the constant production of nucleic acids.

Another aspect of the invention relates to an apparatus for the gentle isolation of clear lysate from a cell suspension containing extra-chromosomal nucleic acids, the apparatus comprising: a first chamber (1) for the cell suspension and a second chamber (2) for the extraction buffer connected to a mixing point (3) by a pump (4), a volume element (5) that connects the mixing point to a vessel, wherein said vessel comprises a means for generating gas bubbles at a location in the bottom of the vessel (6), a gas inlet (7), a clear lysate outlet (8) and neutralization buffer (9).

EXAMPLES

Example 1

Continuous Extraction of E. coli Cells Containing Plasmid Material

For the production of a plasmid-containing clear lysate, 200 g wet weight biomass of E. coli DH5α cells containing a 4.6 kb large high-copy plasmid are resuspended in a 2 L volume of resuspension buffer (50 mM Tris, 10 mM EDTA, pH 8.0). This cell suspension is mixed with extraction buffer by pumping identical volumes of extraction buffer (200 mM NaOH, 1% SDS) and cell suspension through tubes (diameter=10 mm) with a linear flow rate of 830 cm total per minute to a mixing point of both streams. A schematic illustration of this process is presented in FIG. 1. Disruption of the cells occurs within the tubing volume directly following the mixing point. The incubation time is at least 0.27 minutes.

The neutralization of the extracted cell suspension for the precipitation of the cellular components and subsequent non-rigid separation is performed in a simple column by a lateral injection of the cell extract into 2 L neutralization buffer (3 M potassium acetate, acidic acid, pH5.5) with parallel introduction of gas via a wide area from the down-side of the column.

After complete application of the cell suspension to the system and after complete flotation, the bacterial clear lysate is released through an outlet at the lower end side of the vessel.

The resulting optical density (OD) measured at a wavelength of 600 nm ($OD_{600}$) was 0.002. For comparison purposes, a sample of the identical biomass suspension was extracted manually and neutralized. The $OD_{600}$ of this control after centrifugation was 0.07 and after subsequent filtration was 0.03.

Example 2

Continuous Cell Extraction Using Different Flow Rates

For the production of plasmid-containing clear lysate, 200 g wet weight biomass of E. coli DH5α containing a 4.6 kb large high-copy plasmid are resuspended in 2 L resuspension buffer (50 mM Tris, 10 mM EDTA, pH 8.0). This cell suspension is mixed with extraction buffer by pumping identical volumes of extraction buffer (200 mM NaOH, 1% SDS) and cell suspension through tubes (diameter=10 mm) having different linear flow rates, namely, 280, 550, 830, 900, 1080 and 1400 cm per minute to a mixing point of both streams. A schematic illustration of this process is presented in FIG. 1. The cell extraction occurs within the tubing volume directly subsequent to the mixing point.

Figure 2:
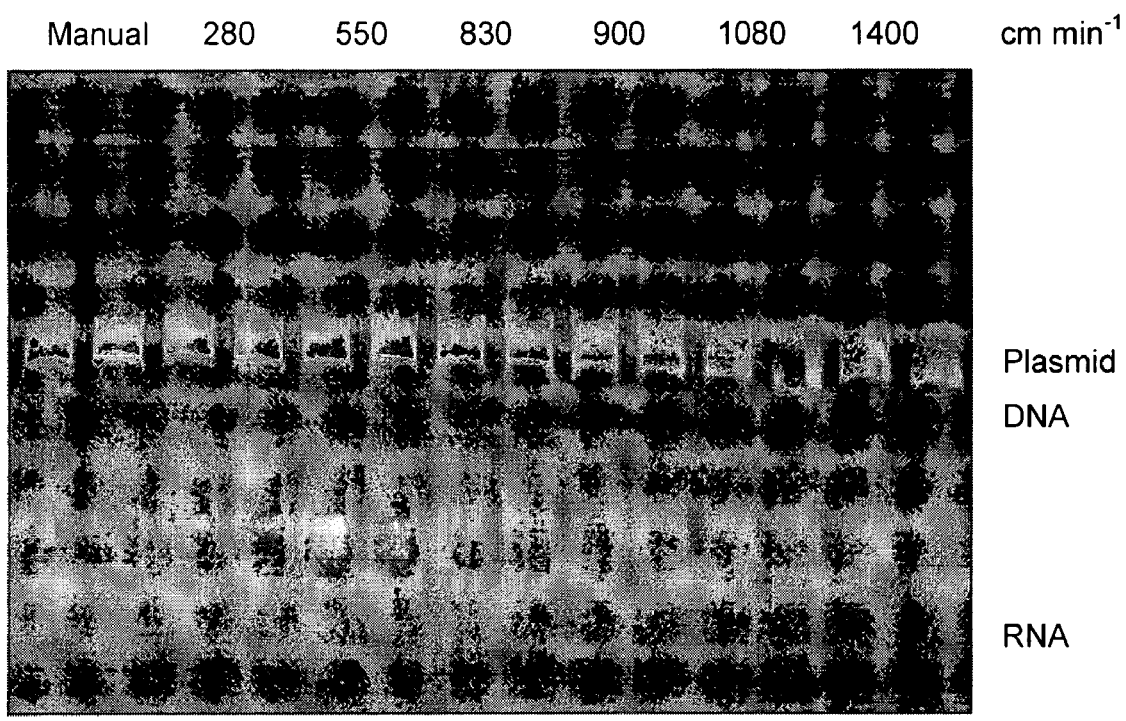
FIG. 2. shows an agarose gel containing a plurality of cell lysates (one lysate per column well) that were extracted using different flow rates.

The neutralization of the extracted cell suspension for the precipitation of the cellular components and subsequent non-rigid separation is performed in a simple vessel via lateral injection of the cell extract into 2 L neutralization buffer (3 M potassium acetate, acidic acid, pH 5.5) with parallel introduction of gas via a wide area from the down-side of the vessel. The resulting lysates were then analyzed by agarose gel electrophoresis (FIG. 2) and were then quantified using capillary gel electrophoresis.

After complete application of the cell suspension to the present system and following complete flotation, the bacterial clear lysate is released through an outlet at the lower end side of the vessel. This release can be performed more rapidly by pumping off the resulting lysate. For comparison, as in Example 1, a sample of the same cell suspension was extracted manually and analyzed. The agarose gel clearly shows the high quality of the plasmid DNA within the clear lysate.

In Table 1, the ratio of the plasmid DNA concentration of the continuously extracted samples to the concentration of the manually extracted reference method is illustrated. The results indicate that flow rates between 280 and 900 cm per minute are sufficient for an efficient cell extraction.

All of the methods and the apparatus disclosed and claimed herein can be made and executed without undue experimentation in light of the present disclosure. While the compositions and methods of this invention have been described in terms of preferred embodiments, it will be apparent to those of skill in the art that variations may be applied to the methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Relative plasmid DNA concentration of a cell lysate according to the flow rate

| Flow Rate / cm min$^{-1}$ | Relative Plasmid Concentration / % |
|---|---|
| Manual | 100 |
| 280 | 86 |
| 550 | 84 |
| 830 | 78 |
| 900 | 99 |
| 1080 | 63 |
| 1400 | 38 |

What is claimed is:

1. A method for producing a microbial clear lysate comprising the steps of:
   (a) mixing a suspension of microorganisms and an extraction buffer at a mixing point, wherein the mixing point is a T-form having at least two inlets opposing each other at an angle of 180° and an outlet that is located perpendicular to and between the two inlets;
   (b) reacting the mixture of step (a) for a duration sufficient to break up the microorganisms, wherein the reacting is performed within a volume element connected directly to the outlet of the mixing point at a linear flow rate of between 280 and 900 cm per minute;
   (c) transferring the mixture of step (b) into a vessel comprising a neutralizing buffer to facilitate the formation of a precipitate and the microbial clear lysate, wherein the precipitate comprises cell debris and genomic DNA and the microbial clear lysate comprises extra-chromosomal nucleic acid; and
   (d) generating gas bubbles by dispersing a gas through the bottom of the vessel to separate the precipitate from the microbial clear lysate by flotation, wherein the gas influx leads to the formation of the gas bubbles to which the precipitate adsorbs thus ascending to form a foam layer on top of the neutralizing buffer.

2. The method according to claim 1, wherein the extra-chromosomal nucleic acid is selected from the group consisting of plasmids, cosmids, BACs, YACs, MACs, mini-plasmids or mincircles.

3. The method according to claim 1, wherein the microorganisms are prokaryotic, eukaryotic cells or vector-transfected cells.

4. The method according to claim 1, wherein the extra-chromosomal nucleic acid stays in solution in the microbial clear lysate.

5. The method according to claim 1, wherein the extraction buffer belongs to the group of an alkaline solution, detergents, enzymes, organic solvents or combinations thereof.

6. The method according to claim 1, wherein the neutralizing buffer is a 3 M solution of potassium acetate and acetic acid at a pH of 5.5.

7. The method according to claim 1, wherein an equal volume of a suspension of microorganisms and an extraction buffer flows into the mixing point.

8. The method according to claim 1, wherein the suspension of microorganisms and the extraction buffer are introduced into the mixing point by a pump.

9. The method according to claim 1, wherein the volume element is a tube, a pipeline or a column.

10. The method according to claim 1, wherein the volume element has a diameter selected from the group consisting of 1.1 cm, 1.2 cm, 1.3 cm, 1.4 cm, 1.5 cm, 1.6 cm, 1.7 cm, 1.8 cm, 1.9 cm, and 2 cm.

11. The method according to claim 1, wherein the volume element has a diameter of between 1.2 cm and 1.6 cm.

12. The method according to claim 1, wherein the duration to break up the microorganisms is at least 0.27 minutes.

13. The method according to claim 1, wherein the vessel is a column or a HPLC column.

14. The method according to claim 1, wherein the gas bubbles of step (d) are generated by dispersing the gas through a frit, a HPLC sieve or a sintered material.

15. The method according to claim 1, wherein the gas bubbles of step (d) are generated by dispersing the gas through a porous material, wherein said porous material has an approximate apparent pore diameter selected from the group consisting of 0.5 µm, 1 µm, 3 µm, 5 µm, 10 µm, 15 µm, 20 µm, 30 µm, 40 µm, 50 µm, 80 µm, 100 µm, 150 µm, 200 µm, 250 µm, 300 µm, 350 µm, 400 µm, 450 µm, 500 µm, 750 µm and less than 1000 µm.

16. The method according to claim 15, wherein the apparent pore diameter is 0.5 µm or 200 µm.

17. The method according to claim 1, wherein the gas is selected from the group consisting of nitrogen, oxygen, carbon dioxide, inert gases, and a combination thereof.

18. The method according to claim 1, wherein steps (a) through (d) are carried out continuously and the microbial clear lysate comprising the extra-chromosomal nucleic acid is constantly removed from the vessel.

19. The method according to claim 1, wherein the dispersion of the gas into the vessel is started prior to transferring the mixture of step (b) into the vessel.

20. The method according to claim 1, wherein the method is carried out utilizing an apparatus, which comprises:
   a first chamber for receiving the suspension of microorganisms and a second chamber for receiving the extraction buffer connected to the mixing point by one or more pumps; and
   ii. the vessel of step (c) connected to the mixing point by the volume element, wherein said vessel comprises a means for generating gas bubbles at a location in the bottom of the vessel, a gas inlet, a microbial clear lysate outlet and the neutralizing buffer.

* * * * *